US005387611A

United States Patent [19]
Rubinstein

[11] Patent Number: 5,387,611
[45] Date of Patent: * Feb. 7, 1995

[54] USE OF BUTYLUREA, NONOXYNOL-9 AND BENZALKONIUM CHLORIDE AS ANTI-BACTERIAL, ANTI-VIRAL CONTRACEPTIVE AGENTS

[75] Inventor: Arye Rubinstein, Monsey, N.Y.

[73] Assignee: Albert Einstein College of Medicine of Yeshiva University, a Division of Yeshiva University, Bronx, N.Y.

[*] Notice: The portion of the term of this patent subsequent to Jul. 20, 2010 has been disclaimed.

[21] Appl. No.: 71,723

[22] Filed: Jun. 3, 1993

Related U.S. Application Data

[63] Continuation-in-part of Ser. No. 847,193, Mar. 6, 1992, Pat. No. 5,229,423.

[51] Int. Cl.⁶ .............. A61K 31/17; A61K 31/14; A61K 31/075
[52] U.S. Cl. .................... 514/588; 514/643; 514/718; 514/843
[58] Field of Search .............. 514/588, 643, 718, 843

[56] References Cited

U.S. PATENT DOCUMENTS

| | | | |
|---|---|---|---|
| 3,813,695 | 6/1974 | Podell, Jr. et al. | 2/168 |
| 4,482,577 | 11/1984 | Goldstein et al. | 427/2 |
| 4,548,844 | 10/1985 | Podell et al. | 428/35 |
| 4,575,476 | 3/1986 | Podell et al. | 428/494 |
| 4,795,761 | 1/1989 | Curtis-Prior et al. | 514/652 |
| 4,880,836 | 11/1989 | Elbaum | 514/588 |
| 4,917,901 | 4/1990 | Bourbon et al. | 424/673 |
| 5,229,423 | 7/1993 | Rubinstein | 514/588 |

Primary Examiner—Raymond J. Henley, III
Assistant Examiner—Kimberly R. Jordan
Attorney, Agent, or Firm—Amster, Rothstein & Ebenstein

[57] ABSTRACT

This invention relates to methods of abrogating sperm motility utilizing the anti-bacterial, anti-viral agents butylurea, Nonoxynol-9 and benzalkonium chloride. This invention is further directed to anti-bacterial, anti-viral, non-irritating contraceptive compositions, and to methods of enhancing contraceptive capabilities of conventional contraceptive means as well as to enhanced conventional contraceptive means.

20 Claims, No Drawings

USE OF BUTYLUREA, NONOXYNOL-9 AND BENZALKONIUM CHLORIDE AS ANTI-BACTERIAL, ANTI-VIRAL CONTRACEPTIVE AGENTS

CROSS REFERENCE TO RELATED APPLICATIONS

This application is a continuation-in-part of application Ser. No. 07/847,193 filed Mar. 6, 1992, now U.S. Pat. No. 5,229,423, which is incorporated herein by reference.

FIELD OF THE INVENTION

This invention relates to the use of butylurea, Nonoxynol-9 and benzalkonium chloride as anti-bacterial, anti-viral contraceptive agents. Specifically, it is directed to the use of butylurea, in combination with Nonoxynol-9 or benzalkonium chloride, or both, as agents for abrogating sperm motility. These agents have anti-bacterial and anti-viral activity, and are non-irritating.

BACKGROUND OF THE INVENTION

U.S. Pat. No. 4,880,836 describes the use of alkylureas as anti-viral agents effective against Herpes I virus, Herpes II virus and the AIDS virus. This patent further describes methods of treating viral infections in media such as blood supply, blood bank and surfaces of all kinds by administering to such media an anti-virally effective amount of alkylurea. However, this patent does not describe the use of any alkylureas, including butylurea, as contraceptive agents.

Several pharmaceutical compositions are currently used as contraceptive agents. For example, Nonoxynol-9 is used as a contraceptive agent in the contraceptive foam Semicid. However, prior hereto, Nonoxynol-9 has been found to be irritating to mucus membranes. For example, 6% Nonoxynol-9 has been shown to cause cervico-vaginal irritation. This irritation increases the risk of HIV-1 infections because it causes a disruption to the vaginal and cervical epithelial cell integrity. See Niruthisard et al. *Sex. Trans. Dis.*, Vol. 18, p. 176 (1991). In further studies, rhesus monkeys exposed to simian immunodeficiency virus were also exposed to a high dose of vaginally-inserted Nonoxynol-9 foam. Half of the monkeys developed simian immunodeficiency virus, thus further indicating that Nonoxynol-9 is not an effective anti-viral agent. See Miller et al., *J. Med. Primatol*, Vol. 19, p. 401 (1990). Hence, Nonoxynol-9, while effective as a contraceptive agent, is irritating to the mucus membranes and is not only not a potent anti-viral agent, but actually serves to increase the risk of viral infection because of its irritant activity.

To date, no compound or composition of compounds have been shown to be both effective anti-bacterial, anti-viral agents as well as effective contraceptive agents which are not irritating to the mucus membranes.

It is therefore an object of this invention to provide methods of abrogating sperm motility utilizing anti-bacterial, anti-viral agents.

It is a further object of this invention to provide compositions which are effective contraceptive agents, which compositions are not irritating to the mucus membranes.

It is another object of this invention to provide non-irritating contraceptive compositions, which compositions are effective in abrogating sperm motility, and which compositions have anti-bacterial and anti-viral activity.

It is still another object of this invention to provide methods of enhancing the contraceptive capabilities of conventional contraceptive means utilizing anti-bacterial, anti-viral, non-irritating contraceptive agents.

It is a still further object of this invention to provide conventional contraceptive means with enhanced contraceptive capabilities.

SUMMARY OF THE INVENTION

This invention is directed to methods of abrogating sperm motility utilizing anti-bacterial, anti-viral non-irritating agents. These agents are butylurea in combination with Nonoxynol-9 and/or benzalkonium chloride. This invention is further directed to methods of enhancing the contraceptive capabilities of conventional contraceptive means as well as to enhanced conventional contraceptive means which have anti-bacterial and anti-viral activity.

DETAILED DESCRIPTION OF THE INVENTION

This invention is directed to methods of abrogating sperm motility utilizing non-irritating agents which have anti-bacterial and anti-viral activity. Specifically 0.2–0.6M preferably 0.4–0.5 M, butylurea is utilized in combination with 0.3–0.6% Nonoxynol-9 and/or benzalkonium chloride. Preferably, benzalkonium chloride is used in a concentration of 0.5% or less. This invention is further directed to anti-bacterial, anti-viral, non-irritating contraceptive compositions comprising 0.2–0.6M (preferably 0.4–0.5M) butylurea in combination with 0.3–0.6% Nonoxynol-9 and/or benzalkonium chloride.

The inventor has discovered than when sperm is put into contact with butylurea at a concentration of 0.2–0.6M in combination with 0.3–0.6% Nonoxynol-9, sperm motility is abrogated. In addition, this combination is non-irritating, and has anti-bacterial and anti-viral activity. Specifically, butylurea has anti-viral activity against HIV-1, HSV-II and Hepatitis B, and has anti-bacterial activity against gram negative bacteria.

Preferably, butylurea is administered at a 0.4–0.5M concentration along with 0.3–0.6% Nonoxynol-9. In addition, 0.2–0.6M butylurea can be used in combination with benzalkonium chloride, preferably at a concentration of 0.5% or less, to broaden the antimicrobial spectrum of the contraceptive agents. Benzalkonium chloride has anti-viral activity against adenovirus 2, vaccinia, influenza A and Herpes Simplex, is non-toxic and has anti-bacterial activity against gram positive bacteria. Further, butylurea, Nonoxynol-9 and benzalkonium chloride can be used in combination as an anti-bacterial, anti-viral, non-irritating contraceptive composition.

These anti-bacterial, anti-viral, non-irritating contraceptive compositions can be used as contraceptive agents which are also effective against sexually transmitted diseases. In addition, butylurea, Nonoxynol-9 and/or benzalkolium chloride can be used as antiseptic disinfectants, for example, on medical equipment or in soaps and other products, and can also be used on dental equipment.

Further, these compositions can be used to enhance the contraceptive capabilities of conventional contraceptive means. These compositions can be used to coat conventional contraceptive means such as condoms, diaphragms or sponges. These compositions can be used in conjunction with a pharmaceutically acceptable carrier, such as a contraceptive foam, or a vaginal foam, to coat conventional contraceptive means.

One method of coating conventional contraceptive means with the anti-bacterial, anti-viral, non-irritating contraceptive compositions of the invention is priming conventional contraceptive means using a priming treatment, such as flame, oxidizing acid, corona discharge or plasma, coating the primed contraceptive means with a liquid solution of hydrogel polymer and absorbing an anti-bacterial, anti-viral, non-irritating contraceptive composition of the invention into the hydrogel polymer. Hydrogel polymer coating methods are discussed in U.S. Pat. Nos. 4,575,476, 4,499,154 and 4,482,577. The coating of conventional contraceptive means with the anti-bacterial, anti-viral, non-irritating contraceptive compositions of the invention will result in enhanced conventional contraceptive means with increased contraceptive capabilities. When sperm is put into contact with such coated contraceptive means, the motility of the sperm is abrogated. In addition, the coated conventional contraceptive means have anti-bacterial and anti-viral activity.

Example

Various contraceptive compositions of this invention were put into contact with hamster eggs and human sperm. Spermicidal activity was determined by measuring penetration of hamster eggs by human sperm after 40 seconds and after 15 minutes. The results are shown in Table I below. Butylurea combinations used were 0.1–0.5M±Nonoxynol-9 at 0.3%.

TABLE I

|  | Spermicidal Activity at 40 Seconds | Spermicidal Activity after 15 Minutes |
| --- | --- | --- |
| 0.1 M Butylurea | incomplete | incomplete |
| 0.2 M Butylurea | incomplete | complete |
| 0.4 M Butylurea | complete | complete |
| 0.5 M Butylurea | complete | complete |
| 0.2 M Butylurea + Nonoxynol-9 diluted 1/20 of 6% solution (= 0.3%) | complete | complete |
| 0.4 M Butylurea + Nonoxynol-9 diluted 1/20 of 6% solution (= 0.3%) | complete | complete |
| 0.2 M Butylurea incorporated in a polymer gel | complete | complete |
| 0.4 M Butylurea incorporated in a polymer gel | complete | complete |

Hence, the inventor has shown that butylurea and Nonoxynol-9 are effective in abrogating sperm motility.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method of abrogating sperm motility comprising putting sperm into contact with 0.2–0.6M butylurea in combination with 0.3–0.6% Nonoxynol-9 and/or benzalkonium chloride.

2. A method of abrogating sperm motility comprising putting sperm into contact with 0.2–0.6M butylurea in combination with 0.3–0.6% Nonoxynol-9 and/or benzalkonium chloride, and a pharmaceutically acceptable carrier.

3. The method according to claim 2 wherein the pharmaceutically acceptable carrier is a contraceptive foam or vaginal foam.

4. The method according to claim 1 wherein the butylurea is 0.4–0.5M.

5. The method according to claim 1 wherein the benzalkonium chloride is 0.5%.

6. A method of abrogating sperm motility utilizing anti-bacterial, anti-viral agents comprising administering 0.2–0.6M butylurea in combination with 0.3–0.6% Nonoxynol-9 and/or benzalkonium chloride.

7. The method according to claim 6 wherein the bacteria is selected from the group consisting of gram positive and gram negative bacteria.

8. The method according to claim 6 wherein the virus is selected from the group consisting of HIV-1, HSV-II, Hepatitis B, adenovirus 2, vaccinia, influenza A and Herpes Simplex.

9. The method according to claim 6 wherein the amount of butylurea in combination with Nonoxynol-9 and/or benzalkonium chloride administered is 0.4–0.5M butylurea, 0.3–0.6% Nonoxynol-9 and 0.5% or less benzalkolium chloride.

10. A contraceptive composition comprising 0.2–0.6M butylurea and 0.3–0.6% Nonoxynol-9.

11. A contraceptive composition 0.2–0.6M butylurea and benzalkonium chloride.

12. A contraceptive composition comprising 0.2–0.6M butylurea in combination with 0.3–0.6% Nonoxynol-9 and benzalkonium chloride.

13. A method of enhancing the contraceptive capabilities of conventional contraceptive means comprising coating a conventional contraceptive means with a contraceptive composition comprising 0.2–0.6M butylurea in combination with 0.3–0.6% Nonoxynol-9 and/or benzalkonium chloride in conjunction with a pharmaceutically acceptable carrier.

14. The method according to claim 13 wherein the pharmaceutically acceptable carrier is a contraceptive or a vaginal foam.

15. The method according to claim 13 wherein the conventional contraceptive means is selected from the group consisting of a condom, a diaphragm or a sponge.

16. The method according to claim 13 wherein the coating of the conventional contraceptive means is performed by priming the conventional contraceptive means with a conventional priming treatment, coating the primed conventional contraceptive means with a liquid solution of hydrogel polymer and absorbing the contraceptive composition into the hydrogel polymer.

17. An enhanced conventional contraceptive means comprising a conventional contraceptive means coated with 0.2–0.6M butylurea in combination with 0.3–0.6% Nonoxynol-9 and/or benzalkonium chloride in conjunction with a pharmaceutically acceptable carrier.

18. The enhanced conventional contraceptive means according to claim 17 wherein the pharmaceutically acceptable carrier is a contraceptive foam or a vaginal foam.

19. The enhanced contraceptive means according to claim 17 wherein the conventional contraceptive means is selected from the group consisting of a condom, a diaphragm or a sponge.

20. An enhanced conventional contraceptive means comprising a contraceptive foam or a vaginal foam and 0.2–0.6M butylurea in combination with 0.3–0.6% Nonoxynol-9 and/or benzalkonium chloride.

* * * * *